(12) United States Patent
Smith

(10) Patent No.: US 7,951,358 B2
(45) Date of Patent: *May 31, 2011

(54) ANTIPERSPIRANT AEROSOL COMPOSITION COMPRISING INERT SILICONES

(75) Inventor: Scott Edward Smith, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 861 days.

This patent is subject to a terminal disclaimer.

(21) Appl. No.: 11/047,168

(22) Filed: Jan. 31, 2005

(65) Prior Publication Data

US 2005/0169851 A1 Aug. 4, 2005

Related U.S. Application Data

(60) Provisional application No. 60/540,930, filed on Jan. 30, 2004.

(51) Int. Cl.
*A61K 8/00* (2006.01)
*A61K 8/89* (2006.01)

(52) U.S. Cl. ............................................. 424/65; 424/47

(58) Field of Classification Search .................. 424/65, 424/68, 400, 401, 59, 47
See application file for complete search history.

(56) References Cited

U.S. PATENT DOCUMENTS

| | | | |
|---|---|---|---|
| 4,152,416 A * | 5/1979 | Spitzer et al. | 424/46 |
| 4,806,338 A | 2/1989 | Smith | |
| 4,822,596 A * | 4/1989 | Callingham et al. | 424/46 |
| 4,863,721 A * | 9/1989 | Beck et al. | 424/47 |
| 4,904,463 A * | 2/1990 | Johnson et al. | 424/44 |
| 5,069,897 A | 12/1991 | Orr | |
| 5,628,989 A * | 5/1997 | Harashima et al. | 424/65 |
| 5,635,165 A | 6/1997 | Panitch | |
| 5,725,836 A | 3/1998 | Rouanet et al. | |
| 5,968,489 A | 10/1999 | Swaile et al. | |
| 6,187,300 B1 | 2/2001 | Motley et al. | |
| 6,503,517 B1 | 1/2003 | Mohammadi et al. | |
| 6,787,603 B2 * | 9/2004 | Johnson et al. | 524/838 |

FOREIGN PATENT DOCUMENTS

| | | | |
|---|---|---|---|
| EP | 0492827 A1 | | 7/1992 |
| GB | 2299024 A | * | 9/1996 |
| GB | 2299507 A | * | 9/1996 |
| WO | WO 98/00097 | | 1/1998 |
| WO | WO 03/002082 A1 | | 1/2003 |

OTHER PUBLICATIONS

USPTO Office Action rejections/objections from co-pending application Case No. CM2812, U.S. Appl. No. 11/046,929; 65 pages.
The most current USPTO Office Action rejections/objections with mail date Mar. 3, 2009 from co-pending application No. CM2812, U.S. Appl. No. 11/046,929; 13 pages.
USPTO Office Action rejections/objections dated Jun. 9, 2009 from co-pending application case No. CM2812, U.S. Appl. No. 11/046,929, inventor Scott Edward Smith, filed Jan. 31, 2005; 16 pages.

* cited by examiner

*Primary Examiner* — Johann R Richter
*Assistant Examiner* — Andriae M Holt
(74) *Attorney, Agent, or Firm* — Mark A. Charles; Andrew J. Hagerty

(57) ABSTRACT

According to a first aspect, antiperspirant concentrate compositions are disclosed comprising particulates of antiperspirant active agent and a silicone component, wherein: (a) the particulates of antiperspirant active agent are the only particulates in the antiperspirant concentrate composition; (b) the silicone component comprises one or more silicones, the or each silicone in the silicone component is inert in relation to the antiperspirant active agent. According to a second aspect, an antiperspirant aerosol composition is provided comprising the antiperspirant concentrate composition according to the first aspect and a propellant. According to a third aspect of the invention, packaged antiperspirant aerosol compositions according to the first aspect are disclosed.

17 Claims, No Drawings

ANTIPERSPIRANT AEROSOL COMPOSITION COMPRISING INERT SILICONES

CROSS REFERENCE TO RELATED APPLICATION

This application claims the benefit of U.S. Provisional Application No. 60/540,930, filed 30 Jan., 2004.

FIELD

The present application concerns an antiperspirant concentrate composition, an antiperspirant aerosol composition and a packaged antiperspirant aerosol composition.

BACKGROUND

The control of underarm wetness has been an issue of varying importance as far back as ancient Egypt and Rome, but it was not until the late 1880's that the first commercial antiperspirant products were introduced, using unbuffered zinc and aluminum compounds. Since then, many strides have been taken in this field and a wealth of antiperspirant products is now available in a wide range of delivery forms, including roll-ons, sticks and aerosol sprays.

The present inventors are primarily concerned with providing improved aerosol spray compositions. Delivery of antiperspirant actives by means of aerosol sprays may suffer from one or more of a number of disadvantages. These can include the necessity to shake the aerosol canister prior to use to achieve an adequate dispersion of active agents, "dustiness" or "powderiness" generated by particulates in the spray, visible residue on the skin and clothing, excessive cooling of the skin on application due to the rapid boiling off of propellant and, last but not least, skin irritation.

Prior investigators in this field have not been idle in recent years: U.S. Pat. No. 5,968,489 addresses the issue of skin irritation and identifies a particular solubiliser for the antiperspirant active that may assist in achieving that objective. WO 03/002082 aims to reduce or solve the problems of dustiness and visible residue by solubilising the active within an anhydrous emulsion.

A disadvantage of compositions taught in the prior art is their unsatisfactory adherence to skin following dispensing. This can result in a large proportion of the antiperspirant active flaking or wicking off leaving only a small amount to do the job it is intended to do. The slightly older teaching found in U.S. Pat. No. 4,806,338 does consider this matter and proposes the use of functionalised siloxanes to overcome it. Functionalised siloxanes proposed by U.S. Pat. No. 4,806,338 can be disadvantageous, however, in that they may react with the antiperspirant active agents, either via an acid-base reaction in the case of aminofunctional silicones, which are Lewis bases (the antiperspirant actives are Lewis acids), or via a chelation reaction (in the case of the carboxy-functional silicones), which reactions can reduce the efficacy of the active. In addition, functional silicones of the type taught by U.S. Pat. No. 4,806,338 may have reduced solubility in the aerosol propellants (and vice versa) which can give rise to inhomogeneity in the product with resultant inhomogeneity of deposition on the target site.

It would be beneficial to provide an antiperspirant aerosol composition that can overcome the above-described disadvantages of the prior art.

SUMMARY

According to a first aspect of the invention, an antiperspirant concentrate composition is provided, comprising particulates of antiperspirant active agent and a silicone component, wherein:
(a) the particulates of antiperspirant active agent are the only solid particulates in the antiperspirant concentrate composition;
(b) the silicone component comprises one or more silicones, the or each silicone in the silicone component being inert in relation to the antiperspirant active agent.

According to a second aspect of the invention, an antiperspirant aerosol composition is provided, comprising particulates of antiperspirant active agent, a propellant and a silicone component, wherein:
(a) the particulates of antiperspirant active agent are the only solid particulates in the antiperspirant aerosol composition;
(b) the silicone component comprises one or more silicones, the or each silicone in the silicone component being inert in relation to the antiperspirant active agent.

Advantageously, according to the second aspect of the invention, the or each silicone in the silicone component is additionally a non-volatile silicone.

According to a third aspect of the invention, a packaged antiperspirant aerosol composition is provided comprising a spray unit within which is comprised an antiperspirant aerosol composition according to the second aspect of the invention.

These and other features, aspects, and advantages of the present invention will become evident to those skilled in the art from a reading of the present disclosure.

As used herein, the phrase "the or each silicone in the silicone component is inert in relation to the antiperspirant active agent" includes silicones which do not measurably chelate with the antiperspirant active agent and, at the same time, are not Lewis bases.

As used herein, the term "non-volatile" used with respect to the silicones includes materials which have a vapor pressure of less than 0.01 mmHg (1.33322 Pa) when measured at 25° C. and have an average boiling point greater than 235° C., preferably greater than 250° C., when measured at 1 Atmosphere (0.101325 Mpa) of pressure.

DETAILED DESCRIPTION

While the specification concludes with claims which particularly point out and distinctly claim the invention, it is believed the present invention will be better understood from the following description.

All weights, measurements and concentrations herein are measured at 25° C. on the composition in its entirety, unless otherwise specified.

Unless otherwise indicated, all percentages of compositions referred to herein are weight percentages of the total composition (i.e. the sum of all components present) and all ratios are weight ratios.

Unless otherwise indicated, all polymer molecular weights are weight average molecular weights.

Unless otherwise indicated, the content of all literature sources referred to within this text are incorporated herein in full by reference.

Except where specific examples of actual measured values are presented, numerical values referred to herein should be considered to be qualified by the word "about".

The present invention relates to antiperspirant aerosol compositions comprising particulate active. Particulate actives enhance dry feel and efficacy on skin and are thus preferred to compositions comprising solubilized active.

The more homogenous an antiperspirant aerosol composition is immediately prior to application, the more homogenous will be the composition actually applied to a consumer's skin and the more uniform will be the cosmetic benefit thereby achieved. Gravity can work hard to destroy homogeneity, however, by causing particulates to settle out of antiperspirant aerosol compositions. To mitigate this problem, consumers are advised to shake the spray canister before use, but this is annoying and, in cases of extreme settling, it may not be sufficient. To reduce settling, a number of approaches may be employed, such as the inclusion of so-called "bulking agents" or "suspending agents" which act by thickening the formulation and reducing the settling rate. On another level, bulking agents can be regarded to act by filling the void space between suspended particles. Examples of bulking agents include hydrophobically treated montmorillonite clay such as bentonite and/or hectorite and some silicas. The hectorite and bentonite clays have a layered clay structure which expands or swells on contact with polar liquids, such as water, ethanol, propylene carbonate and mixtures of these materials. Bulking agents can contribute to a number of perceived disadvantages, however, including residue on skin and clothing. As a result of the above-mentioned disadvantages, the present inventors have moved away from the inclusion of bulking agents and combat the problem of active settling by including high viscosity polymeric material in the composition thus increasing the overall viscosity of the final product to reduce the settling rate. In addition, to minimise settling problems altogether, the present compositions comprise no solid particulates other than the antiperspirant active particles.

In addition to improving the consistency and reducing the dustiness of the composition, a further objective of the present inventor was to improve the efficiency of the composition. This is primarily achieved, according to the present invention, by ensuring that particulates of active agent do not react with or chelate with the silicone component. Further improvements in efficiency may be achieved by ensuring that as much of the active agent as possible stays at the application site. A yet further objective of the inventor was to improve the cosmetics of the product by reducing residues on skin and clothes.

Traditionally, antiperspirant aerosol sprays have incorporated silicones to provide lubrication and to improve the adherence of the particulate active agents to the skin. Historically, these silicone materials tended to be volatile silicone oils. It has now been established, however, that evaporation of the volatile oils following application can reduce the tendency of the active agents to adhere to the skin with time to a surprising degree, thereby allowing the particulates to become detached following just minor motion or abrasion by clothing not long after application. The present inventors have also learned that this tendency may be significantly reduced when non-volatile fluids are employed in place of the volatile oils—by so doing a far greater percentage of the active agent may be retained on the skin for a longer period of time to perform the task it is there to do. Furthermore, volatile silicone oils are lower in viscosity than the non-volatile fluids to the extent that compositions containing them may require additional thickening to reduce the problem of settling, discussed above. That thickening was often achieved by means of bulking agents, with the attendant disadvantages such as the formation of visible residues, also discussed above. In summary, according to an advantageous embodiment of the invention, non-volatile silicone fluids are used in place of volatile ones resulting in improved adhesion of the active agents over time and reduction of residues.

Antiperspirant aerosol compositions according to the invention may advantageously comprise from 1% wt to 25% wt, preferably from 3% wt to 20% wt and more preferred from 5% wt to 15% wt antiperspirant active.

The particulate antiperspirant active materials of this invention may comprise any compound or composition having antiperspirant activity. Astringent metallic salts are preferred antiperspirant materials for use herein, particularly including the inorganic and organic salts of aluminum, zirconium and zinc, and mixtures thereof. More preferred antiperspirant actives according to the present invention include aluminum and zirconium salts such as aluminum halides, aluminum hydroxide halides, zirconyl oxide halides, zirconyl hydroxy halides, and mixtures thereof. Yet more preferred are basic aluminium salts, since a number of the other types of salt, such as those of zirconium, give rise to inhalation safety concerns in an environment.

Advantageously the aluminum salts include those of the formula

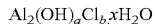

$$Al_2(OH)_aCl_b \cdot xH_2O$$

wherein a is from about 2 to about 5; a+b=6; x is from about 1 to about 6; and wherein a, b, and x may have non-integer values. Particularly preferred are aluminum chlorhydroxides referred to as "⅚ basic chlorhydroxide", wherein a=5, and "⅔ basic chlorhydroxide," wherein a=4.

Antiperspirant aerosol compositions according to the invention comprise at least 1%, preferably from 1% to 40% by weight of the entire antiperspirant aerosol composition of silicone component. The or each silicone comprised within the silicone component is inert in relation to the antiperspirant active agent, in the sense that it does not measurably chelate with the antiperspirant active agent and is not a Lewis base.

Advantageously, the silicone component comprises less than 25%, preferably less than 10%, more preferably less than 5% volatile silicones by weight of the silicone component. More preferably still, the silicone component comprises no volatile silicones such that the or each silicone in the silicone component is a non-volatile silicone. As used herein, the term "volatile" when used with respect to the silicones includes all silicones not defined as "non-volatile", above.

In one advantageous embodiment, the antiperspirant aerosol composition more preferably comprises from 1 to 10% wt, yet more preferably from 2 to 8.5% wt and more preferably still from 3 to 6% wt silicone component. In some jurisdictions where strict limits are placed on the maximum amount of propellant present in the formulation, the antiperspirant aerosol composition may, according to another embodiment, comprise from 15 to 40% wt, yet more preferably from 20 to 35% wt and more preferably still from 25 to 35% wt silicone component.

Silicones which may be included in the antiperspirant aerosol compositions according to the invention include silicone gums, silicone waxes and silicone oils which may be functionalised or non-functionalised, provided that they are also inert, as defined herein.

Silicone gums which may be incorporated in antiperspirant aerosol compositions according to the invention include linear silicone gums with a molecular weight from about 140,000 to 350,000 and branched-chain silicone gums having a molecular weight from 140,000 to about 2,000,000.

Preferred silicone gums include dimethyl polysiloxane (PDMS) type gums.

Silicone oils which may be incorporated in antiperspirant aerosol compositions according to the invention include those having a viscosity from 0.005 $Nsm^{-2}$ to 1000 $Nsm^{-2}$ (5 to 1,000,000 centipoise) measured on a Brookfield Viscometer using an appropriate spindle at the appropriate RPM range at 25° C. (the RPM range and/or spindle is adjusted by a person skilled in the art according to the viscosity of the material, with highly viscous materials being measured at lower RPMs than and with different spindles from low viscosity materials. This does not affect the final viscosity reading, but is needed to keep that reading on the Viscometer scale).

Examples of commercially available non-volatile silicone oils suitable for use in the antiperspirant compositions include, but are not limited to: Dow Corning 200, hexamethyldisiloxane, Rhodorsil Oils 70047 available from Rhone-Poulenc, Masil SF Fluid available from Mazer, Dow Corning 225, Dow Corning 1732, Dow Corning 5732, Dow Corning 5750 (available from Dow Corning Corp.); 34720, 34749, 34731 and 33134, SF-96, SF-1066 and SF18(350) Silicone Fluids (available from G. E. Silicones); Silicone L-45, Silicone L530, Silicone L-531 (available from Union Carbide) and Siloxane F-221 and Silicone Fluid SWS-101 (available from SWS Silicones).

Examples of commercially available non-volatile silicone gums suitable for use in the antiperspirant compositions include, but are not limited to: SE30 and SE 32, both produced by GE.

Examples of commercially available non-volatile silicone waxes suitable for use in the antiperspirant compositions include, but are not limited to 5201 and 5203, both from Dow Corning.

Antiperspirant aerosol compositions according to the invention may comprise emollient. Advantageously, the emollient is present in an amount from 0.1% wt to 10% wt, preferably from 0.1% wt to 5% wt and more preferred from 0.25% wt to 3.5% wt of the antiperspirant aerosol composition. Emollients materials may be added to enhance the feel of the products and the resulting skin feel following application.

Emollients which may be included according to the invention include hydrocarbon oils, waxes and oil soluble vitamins. Suitable hydrocarbon oils according to the invention include mineral oil; suitable oil-soluble vitamins according to the invention include Vitamin E; suitable waxes according to the invention include natural and synthetic waxes. The class of natural waxes includes animal waxes, such as beeswax, lanolin, shellac wax and Chinese insect wax; vegetable waxes, such as carnauba, candelilla, bayberry and sugar cane; mineral waxes, such as ceresin and ozokerite; petrochemical waxes, such as microcrystalline wax and petrolatum. The class of synthetic waxes includes ethylenic polymers and polyol ether-esters, chlorinated naphthalenes and Fischer-Tropsch waxes. For more details, please refer to see Römpp Chemie Lexikon, Georg Thieme Verlag, Stuttgart, $9^{th}$ Edition, 1995 under "Wachse".

The emollients according to the invention may include silicones, such as silicone waxes. In that case, however, those silicones are inert, as defined above, and they form part of the silicone component.

Antiperspirant aerosol compositions according to the invention may advantageously comprise active release agents that assist the active in being released from the silicone matrix onto the skin. These active release agents include aliphatic polyhydric alcohols having from 2 to 12 carbon atoms, examples of which include propylene glycol, ethylene glycol, diethylene glycol, butylene glycol, 1,2-proplyene glycol, 1,3-propylene glycol, 1,3-butylene glycol (1,3-butane-diol), glycerine (1,2,3-trihydroxy propane), 2-methyl-2,4-pentanediol (hexylene glycol), 2-ethyl-1,3-hexane-diol, 1,2,6-hexanetriol, and combinations thereof. Advantageously, active release agents may be added to the composition in an amount from 0.01% wt to 10% wt, more preferred from 0.5% wt to 7% wt and more preferably still from 1% wt to 3% wt.

A certain amount of bound and unbound water is associated with the antiperspirant active particulates—the precise amounts depending upon how hygroscopic that active material is. Advantageously, the levels of that water will be balanced in order that, when the particulate antiperspirant active is placed in a highly nonpolar environment (such as that found in an antiperspirant aerosol composition), agglomeration is minimised. It has been found that, by adding a quaternary ammonium functional silicones to the formulation, the agglomeration can be mitigated. Any quaternary ammonium functional silicones that is soluble in the propellant may be employed. Advantageously the quaternary ammonium functional silicone in included in the antiperspirant aerosol composition at a level from 0.01% wt to 25% wt, preferably from 0.1% wt to 10% wt and more preferably from 0.5% wt to 2% wt.

Quaternary ammonium functional silicones which may be included in antiperspirant aerosol compositions according to the invention include silicone based quaternary ammonium functional silicones comprising the group: —$R^1$—Z-$Q^3$, where, —$R^1$— is either a divalent hydrocarbon group, which may optionally incorporate ether or ester functionality, or —$R^2N(Q^1)R^3$—, and is covalently bonded to Si in an unsupported silicone or silane; —Z— is —C(O)O— or —N($Q^2$)-; -$Q^3$ is —CH($R^4$)CH(OH)YN$^+$($R^5$)($R^6$)($R^7$)X$^-$, or a monovalent hydrocarbon group that may optionally incorporate hydroxy, diol, amide, ether or ester functionality; —$R^2$— and —$R^3$— are independently divalent hydrocarbon groups that may optionally incorporate ether or ester functionality; -$Q^1$ and -$Q^2$ are independently —CH($R^4$)CH(OH)YN$^+$($R^5$)($R^6$)($R^7$)X$^-$, or a monovalent hydrocarbon group that may optionally incorporate hydroxy, diol, amide, ether or ester functionality; Y is a divalent hydrocarbon group; $R^4$ is a monovalent hydrocarbon group or hydrogen; $R^5$, $R^6$ and $R^7$ are independently monovalent hydrocarbon groups; and X$^-$ is a counter ion, with the proviso that at least one of -$Q^1$, $Q^2$ and -$Q^3$ is —CH($R^4$)CH(OH)YN$^+$($R^5$)($R^6$)($R^7$)X$^-$.

A preferred quaternary ammonium silicone polymer is supplied within the 5-7113 emulsion by Dow Corning and has the CAS number 495403-02-6.

If quaternary ammonium functional silicones are included in the antiperspirant aerosol compositions according to the invention, then those silicones are inert, as defined above, and they form part of the silicone component.

The propellant concentration in the antiperspirant aerosol composition may advantageously range from 20% to 90%, preferably from 40% to 85%, more preferably from about 55% to 80% by weight of the antiperspirant aerosol composition.

The propellant comprises one or more volatile materials, which in a gaseous state, carry the other components of the present invention in particulate or droplet form. The aerosol propellants useful in the present invention typically have a boiling point within the range of from about −45° C. to about 5° C. The aerosol propellants are liquefied when packaged in conventional aerosol containers under pressure. The rapid boiling of the aerosol propellant upon leaving the aerosol container aids in the atomization of the other components of the present invention.

Aerosol propellants which may be employed in compositions according to the present invention include the chemically-inert hydrocarbons such as propane, n-butane, isobutane and cyclopropane, and mixtures thereof, as well as halogenated hydrocarbons such as dichlorodiluoromethane (propellant 12) 1,1-dichloro-1,1,2,2-tetrafluoroethane (propellant 114), 1-chloro-1,1-difluoro-2,2-trifluoroethane (propellant 115), 1-chloro-1,1-difluoroethylene (propellant 142B), 1,1-difluoroethane (propellant 152A), dimethyl ether and monochlorodifluoromethane, and mixtures thereof. Preferably, the propellant incorporated into the antiperspirant aerosol composition according to the invention comprises hydrocarbons, such as isobutane, propane and butane. These materials are preferred due to their low ozone reactivity. These hydrocarbons may be used as individual components where their vapor pressures at 21.1° C. (70° F.) range from 1.17 to 7.45 Bar (17 psig to 108 psig). The preferred components as individuals or mixtures range in pressure from about 1.17 to 4.83 Bar (17 to about 70 psig) and more preferably from 2.14 to 3.79 Bar (31 and 55 psig).

Compositions according to the invention may additionally comprise perfume, the amount depending on consumer preferences around the time of manufacture. Advantageously, at the present time, compositions according to the invention may comprise from 0.05% wt to 5% wt, preferably from 0.5% wt to 3% wt and more preferably from 1% wt to 2% wt perfume.

According to a second aspect of the invention, packaged antiperspirant aerosol compositions are provided, comprising a spray unit within which is comprised an antiperspirant aerosol composition according to the first aspect of the invention. The spray unit may be any spray unit suitable for containing antiperspirant aerosol compositions according to the invention.

The following examples further describe and demonstrate the preferred embodiments within the scope of the present invention. The examples are given solely for the purpose of illustration, and are not to be construed as limitations of the present invention since many variations thereof are possible without departing from its scope.

EXAMPLES

The compositions disclosed in the below examples were all made using the following general method: silicone fluid was added under agitation to an appropriately sized container. Other silicone components (if present) were then added and the mixture was stirred until uniform. At this point, non-silicone based emollient (if present) was added and the mixture was stirred until uniform, under increased temperature (which may vary, due to differing melting points) to ensure uniformity, if appropriate. The active particulates were added to the mixture at this stage under mixing to achieve a uniform consistency. In compositions in comprising materials, such as waxes, which are not soluble in the silicone component, the temperature was maintained at an appropriate level. Lastly, the desired weight of this mixture (antiperspirant concentrate composition) was transferred to the finished unit, the desired valve was affixed and propellant was added to the finished unit. A propellant known as A46 was used, which is a mixture of 85% isobutane and 15% propane.

| | | Example 1 | Example 2 | Example 3 | Example 4 | Example 5 | Example 6 | Example 7 |
|---|---|---|---|---|---|---|---|---|
| Aluminum Chlorohydrate | Reheis Macro 95 | 1.00% | 3.00% | 3.00% | 15.00% | 15.00% | 15.00% | 25.00% |
| Dow 200 Fluid | 10 cps | 1.00% | | | | 15.00% | | 20.00% |
| Dow 200 Fluid | 50 cps | | | | 6.00% | | | |
| Dow 200 Fluid | 350 cps | | | 2.00% | | | | |
| General Electric 34749 CRDV946LV | 18 M cps | | | | | | 10.00% | |
| General Electric 34720 CRTV50M | 50 M cps | | 1.00% | | | | | |
| General Electric 34731 CRTV940 | 116 M cps | | | | | 1.00% | | |
| General Electric 33134 81536 | 1.25 MM cps | | | | | | | |
| Gereral Electric SE30 | 30–50 MM cps | 0.10% | 0.10% | | 1.00% | 0.50% | | |
| Dow 7-6030 quaternary silicone | Polymer only | 0.10% | | | | 0.25% | | 10.00% |
| Superwhite petrolatum | Witco chemical | 0.40% | 1.00% | 0.50% | | 0.50% | 2.00% | |
| Propellant | A46 | 97.40% | 94.90% | 94.50% | 78.00% | 67.75% | 73.00% | 45.00% |
| TOTAL | | 100.00% | 100.00% | 100.00% | 100.00% | 100.00% | 100.00% | 100.00% |

| | | Example 8 | Example 9 | Example 10 | Example 11 | Example 12 | Example 13 | Example 14 |
|---|---|---|---|---|---|---|---|---|
| Aluminum Sesqui-Chlorohydrate | Reheis 314 | 25.00% | 5.00% | 5.00% | 10.00% | 10.00% | 15.00% | 15.00% |

-continued

| | | | | | | | | |
|---|---|---|---|---|---|---|---|---|
| Dow 200 Fluid | 10 cps | | 5.00% | | | | | 5.00% |
| Dow 200 Fluid | 50 cps | | | 10.00% | | | | 5.00% |
| Dow 200 Fluid | 350 cps | | | 5.00% | | | | |
| General Electric 34749 CRDV946LV | 18 M cps | | | | | | 6.50% | 2.00% |
| General Electric 34720 CRTV50M | 50 M cps | | | | | | | 1.00% |
| General Electric 34731 CRTV940 | 116 M cps | | | | | | | 3.00% |
| General Electric 33134 81536 | 1.25 MM cps | | | | | 5.00% | | 0.50% |
| Gereral Electric SE30 | 30–50 MM cps | | | 0.50% | | 0.25% | 0.10% | |
| Dow 7-6030 quaternary silicone | Polymer only | 20.00% | 2.00% | | 1.00% | 0.10% | 0.15% | |
| Superwhite petrolatum | Witco chemical | | 3.00% | | 2.00% | 0.50% | 1.50% | |
| Propellant | A46 | 55.00% | 85.00% | 79.50% | 82.00% | 82.65% | 76.75% | 75.00% |
| TOTAL | | 100.00% | 100.00% | 100.00% | 100.00% | 100.00% | 100.00% | 100.00% |

| | | Example 15 | Example 16 | Example 17 | Example 18 | Example 19 | Example 20 | Example 21 |
|---|---|---|---|---|---|---|---|---|
| Aluminum Di-Chlorohydrate | Reheis R-315 | 20.00% | 20.00% | 25.00% | 5.00% | 5.00% | 10.00% | 10.00% |
| Dow 200 Fluid | 10 cps | | 1.00% | 15.00% | 4.00% | | 3.00% | 7.00% |
| Dow 200 Fluid | 50 cps | | | 5.00% | | | | |
| Dow 200 Fluid | 350 cps | 20.00% | | 3.00% | | 5.32% | | 3.00% |
| General Electric 34749 CRDV946LV | 18 M cps | | | 5.90% | | | | |
| General Electric 34720 CRTV50M | 50 M cps | | | | | | 1.00% | |
| General Electric 34731 CRTV940 | 116 M cps | | 5.00% | | | | 1.00% | |
| General Electric 33134 81536 | 1.25 MM cps | | | | | | 1.00% | |
| Gereral Electric SE30 | 30–50 MM cps | | | 0.10% | 1.32% | | 0.10% | |
| Dow 7-6030 quaternary silicone | Polymer only | 0.10% | | 3.00% | | | 0.20% | 1.00% |
| Superwhite petrolatum | Witco chemical | | | 3.00% | 0.40% | 0.40% | 0.40% | 1.00% |
| Propellant | A46 | 59.90% | 74.00% | 40.00% | 89.28% | 89.28% | 83.30% | 78.00% |
| TOTAL | | 100.00% | 100.00% | 100.00% | 100.00% | 100.00% | 100.00% | 100.00% |

| | | Example 22 | Example 23 | Example 24 | Example 25 | Example 26 |
|---|---|---|---|---|---|---|
| Aluminum Di-Chlorohydrate | Reheis R-315 | 15.00% | 15.00% | 20.00% | 20.00% | 25.00% |
| Dow 200 Fluid | 10 cps | | 1.00% | 5.00% | 4.00% | |
| Dow 200 Fluid | 50 cps | 15.00% | 1.00% | | | |
| Dow 200 Fluid | 350 cps | | 2.00% | 5.00% | | 6.40% |
| General Electric 34749 CRDV946LV | 18 M cps | | 0.50% | | | |

| | | | | | |
|---|---|---|---|---|---|
| General Electric 34720 CRTV50M | 50 M cps | | 0.50% | | |
| General Electric 34731 CRTV940 | 116 M cps | | 0.50% | | |
| General Electric 33134 81536 | 1.25 MM cps | | 0.50% | | 1.00% | 0.50% |
| Gereral Electric SE30 | 30–50 MM cps | | 0.10% | | 0.25% | 0.10% |
| Dow 7-6030 quaternary silicone | Polymer only | 0.50% | 0.15% | | | 5.00% |
| Superwhite petrolatum | Witco chemical | 0.50% | 0.40% | | 0.50% | 3.00% |
| Propellant | A46 | 69.00% | 78.35% | 70.00% | 74.25% | 60.00% |
| TOTAL | | 100.00% | 100.00% | 100.00% | 100.00% | 100.00% |

It is understood that the examples and embodiments described herein are for illustrative purposes only and that various modifications or changes in light thereof will be suggested to one skilled in the art without departing from the scope of the present invention.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An antiperspirant aerosol composition, comprising:
   a) particulates of antiperspirant active agent;
   b) a propellant; and
   c) 1% to 40% by weight, based on the total weight of the antiperspirant aerosol composition, of a silicone component comprising a non-volatile silicone oil and a quaternary ammonium functional silicone, wherein the silicone component comprises no volatile silicones, and wherein the silicone component is devoid of functionalized siloxanes that are capable of reacting with the antiperspirant active agent via an acid-base reaction or a chelation reaction,
   wherein the particulates of antiperspirant active agent are the only solid particulates in the antiperspirant aerosol composition,
   wherein said silicone component further comprises a silicone gum, a silicone wax, or both.

2. The antiperspirant aerosol composition of claim 1, comprising 15% to 40% by weight of said silicone component, based on the total weight of said antiperspirant aerosol composition.

3. The antiperspirant aerosol composition of claim 1, wherein said non-volatile silicone oil is selected from those having a viscosity from about 0.005 $Nsm^{-2}$ to about 1000 $Nsm^{-2}$ measured at about 25° C.

4. The antiperspirant aerosol composition of claim 1, wherein said silicone gum is selected from the group consisting of linear silicone gums having a molecular weight from about 140,000 to about 350,000, branched chain silicone gums having a molecular weight from about 140,000 to about 2,000,000 and mixtures thereof.

5. The antiperspirant aerosol composition of claim 1, wherein the antiperspirant active has the following general formula:

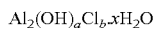

$Al_2(OH)_aCl_b \cdot xH_2O$ wherein a is from about 2 to about 5; a+b=6; x is from about 1 to about 6; and
wherein a, b, and x may have non-integer values.

6. The antiperspirant aerosol composition of claim 5, wherein a=5.

7. The antiperspirant aerosol composition of claim 5, wherein a=4.

8. The antiperspirant aerosol composition of claim 1, comprising from about 5% to about 15% antiperspirant active agent by weight of the antiperspirant aerosol composition.

9. The antiperspirant aerosol composition of claim 1 additionally comprising emollient.

10. The antiperspirant aerosol composition of claim 9 comprising from about 0.1% to about 5% by weight of the antiperspirant aerosol composition of emollient.

11. The antiperspirant aerosol composition of claim 9 comprising from about 0.25% to about 3.5% by weight of the antiperspirant aerosol composition of emollient.

12. The antiperspirant aerosol composition of claim 9, wherein the emollient is petrolatum.

13. The antiperspirant aerosol composition of claim 1 further comprising an active release agent, the active release agent comprising an aliphatic polyhydric alcohol having from 2 to 12 carbon atoms.

14. The antiperspirant aerosol compositions of claim 13, wherein active release agent is selected from the group consisting of propylene glycol, ethylene glycol, diethylene glycol, butylene glycol, 1,2-propylene glycol, 1,3-propylene glycol, 1,3-butylene glycol, glycerine, 2-methyl-2,4-pentane-diol, 2-ethyl-1,3-hexane-diol, 1,2,6-hexanetriol and mixtures thereof.

15. The antiperspirant aerosol composition of claim 13 comprising from about 0.01 to about 10% by weight of the antiperspirant aerosol composition of active release agent.

16. Antiperspirant aerosol composition of claim 1 wherein the propellant is selected from the group consisting of propane, n-butane, isobutane and cyclopropane, halogenated hydrocarbons and mixtures thereof.

17. Antiperspirant aerosol composition of claim 16 wherein the halogenated hydrocarbon is selected from the group consisting of dichlorodifluoromethane, 1,1-dichloro-1, 1,2,2-tetrafluoroethane, 1-chloro-1,1-difluoro-2,2-trifluoroethane, 1-chloro-1,1-difluoroethylene (propellant 142B), 1,1-difluoroethane, and monochlorodifluoromethane and mixtures thereof.

* * * * *